US009393563B2

United States Patent
Kim et al.

(10) Patent No.: US 9,393,563 B2
(45) Date of Patent: Jul. 19, 2016

(54) STRIP FOR LATERAL FLOW ASSAY, COMPRISING SUBPAD, AND CARTRIDGE FOR LATERAL FLOW ASSAY USED FOR THE SAME

(71) Applicant: BODITECH MED. INC., Chuncheon-si, Gangwon-do (KR)

(72) Inventors: Byeong Chul Kim, Chuncheon-si (KR); Ki Tae Park, Chuncheon-si (KR); Hyun Jeong Kim, Chuncheon-si (KR)

(73) Assignee: BODITECH MED. INC, Gangwon-Do (KR)

( * ) Notice: Subject to any disclaimer, the term of this patent is extended or adjusted under 35 U.S.C. 154(b) by 0 days.

(21) Appl. No.: 14/435,988

(22) PCT Filed: Oct. 15, 2013

(86) PCT No.: PCT/KR2013/009174
§ 371 (c)(1),
(2) Date: Apr. 15, 2015

(87) PCT Pub. No.: WO2014/061954
PCT Pub. Date: Apr. 24, 2014

(65) Prior Publication Data
US 2015/0251177 A1 Sep. 10, 2015

(30) Foreign Application Priority Data
Oct. 16, 2012 (KR) .......................... 10-2012-0114508

(51) Int. Cl.
*G01N 21/75* (2006.01)
*B01L 3/00* (2006.01)
(Continued)

(52) U.S. Cl.
CPC ................. *B01L 3/5023* (2013.01); *B01L 9/06* (2013.01); *G01N 33/54386* (2013.01);
(Continued)

(58) Field of Classification Search
CPC ............ B01L 3/5023; B01L 2200/026; B01L 2300/045; B01L 2300/0681; B01L 2300/069; B01L 2300/0825; B01L 2300/089; B01L 2400/0406; G01N 33/53; G01N 33/54386; G01N 33/558
See application file for complete search history.

(56) References Cited

U.S. PATENT DOCUMENTS

| 2002/0001854 A1* | 1/2002 | Lee ........................ B01L 3/5023 436/518 |
| 2005/0106750 A1* | 5/2005 | Tung .................... A61B 10/007 436/169 |
| 2012/0220049 A1 | 8/2012 | Bunce et al. ................... 436/501 |

FOREIGN PATENT DOCUMENTS

| KR | 10-0910982 B1 | 8/2009 |
| KR | 10-1149357 B1 | 5/2012 |
| WO | WO 2011/069031 A2 | 6/2011 |

OTHER PUBLICATIONS

International Search Report dated Nov. 7, 2013, issued to the corresponding International Application No. PCT/KR2013/009174.

*Primary Examiner* — Dennis M White
(74) *Attorney, Agent, or Firm* — Stein IP, LLC

(57) ABSTRACT

The present application relates to: a strip for lateral flow assay, comprising a support, a medium for development, a sample pad comprising a subpad, and an absorption pad; and a cartridge for lateral flow assay, comprising the same. According to the present application, the strip adopts a novel sample loading method, thereby obtaining reproducible results irrespective of the volume of an injected sample, and it is possible to readily change the amount of a sample, as necessary, thereby improving the reproducibility of measured results and convenience.

5 Claims, 14 Drawing Sheets

(51) Int. Cl.
   *G01N 33/558* (2006.01)
   *G01N 33/543* (2006.01)
   *B01L 9/06* (2006.01)
(52) U.S. Cl.
   CPC ........ *G01N 33/558* (2013.01); *B01L 2200/026* (2013.01); *B01L 2300/045* (2013.01); *B01L 2300/069* (2013.01); *B01L 2300/0681* (2013.01); *B01L 2300/089* (2013.01); *B01L 2300/0825* (2013.01); *B01L 2300/0851* (2013.01); *B01L 2300/123* (2013.01); *B01L 2300/16* (2013.01); *B01L 2400/0406* (2013.01)

(a)

(b)

STRIP FOR LATERAL FLOW ASSAY, COMPRISING SUBPAD, AND CARTRIDGE FOR LATERAL FLOW ASSAY USED FOR THE SAME

CROSS-REFERENCE TO RELATED APPLICATIONS

This application is a national stage of International Application No. PCT/KR2013/009174, filed Oct. 15, 2013, which claims the benefit of Korean Application No. 10-2012-0114508, filed Oct. 16, 2012, in the Korean Intellectual Property Office. All disclosures of the documents named above are incorporated herein by reference.

BACKGROUND OF THE INVENTION

1. Field of the Invention

The present disclosure relates to a strip used for analyzing sample and a cartridge for the same.

2. Description of the Related Art

Diagnostic methods and devices for qualitative or quantitative measurement of a finite amount of materials in biological samples such as blood or urine have been developed for the last 30 years. Since an introduction of radioimmunoassay (RIA) using radioisotopes in the 1950s, other assays such as enzyme-linked immunosorbent assays (ELISA) were also developed in the 1970s and 1980s.

For the analysis of proteins, immunological methods based on an antigen-antibody reaction such as ELISA and immunochromatography have been widely used. However, it requires a considerable amount of time to prepare samples and to analyze them.

For the analysis of nucleic acids, it is important to detect the presence of a particular DNA or RNA sequence of interest in the sample. Examples of such methods include the Southern or Northern blot analyses using a probe amplified by a polymerase chain reaction. However, it requires a considerable amount of time to analyze in addition to problems such as repeated experiments are required to find an optimal condition for accurate and reproducible results. Furthermore, the results are subject to external conditions such as time, temperature, composition of nucleic acid sequence employed for the hybridization, which requires the involvement of well-trained experts for the analysis.

Particularly, in the case where accurate detection results are imperative for a reliable diagnosis, there is a need to develop methods, which can produce accurate, reliable and reproducible results with high sensitivity and specificity in a relatively short period of time. For example, the diagnosis cervical cancer, which relies on the nucleic acid detection, is on the rise. There are needs to develop detection system, which is able to provide a more sensitive and reliable results in a rapid and convenient manner to replace the conventional system.

One of the recently developed methods to detect nucleic acids or proteins in a sample is a lateral flow assay based on chromatography. The lateral flow assay is widely used in a variety of fields such as pregnancy test and cancer diagnosis to detect proteins, nucleic acids or microorganisms.

Korean Patent No. 1115014 relates to a chromatography system to detect nucleic acids and discloses a strip comprising a solid support, a chromatographic medium, a sample pad and an absorption pad. When an aliquot of sample is loaded to the sample pad, the sample moves through the chromatographic medium to the absorption pad by capillary action during which a component of interest in the sample binds to capturing nucleic acids immobilized on the medium. In such a conventional strip, exact amount of samples are loaded directly onto a sample pad to obtain a reproducible result. Thus samples to be loaded need to be measured as accurately as one microliter unit, which leads to the inconveniences to the user and is the cause for error in the detection results. Further changes in the amount of sample to be loaded should be accompanied by corresponding changes in the structures of the strips and cartridges therefor.

DETAILED DESCRIPTION OF THE INVENTION

Problems to be Solved

The present invention is to provide a strip and a cartridge for a lateral flow assay that can provide accurate and reproducible results, which are not influenced by the differences, or variations in the amount of sample applied which inevitably arise from various reasons.

SUMMARY OF THE INVENTION

In one aspect, the present disclosure provides a strip for a lateral flow assay comprising a solid support, a chromatographic medium, a sample pad with a subpad and an absorption pad. The chromatographic medium, the sample pad with a subpad and the absorption pad being positioned on the solid support in the same plane to permit a capillary flow. The sample pad and the absorption pad each being positioned on each one end of the solid support with the chromatographic medium being located in-between.

In one embodiment, the subpad comprises a body portion, a slant extended from the body portion and a dipping portion extended from the slant.

In other embodiment, the width of the dipping portion of the subpad is wider than that of the strip.

In still other embodiment, the subpad takes a form which is integrated with the sample pad or a form which is detachable from the sample pad. The material for subpad or sample pad can be different or the same.

In still other embodiment, the subpad is configured to be integrated with the sample pad in such a way that the body portion of the subpad also functions as a sample pad, in which case no separate sample pad is provided.

In still other embodiment, the subpad is configured to be detachable from the sample pad and the subpad can function as a filter unit to remove impurities contained in a sample by a capillary action.

In still other embodiment, the length of the absorption pad may be controlled or determined to obtain an optimal result, the length of which may be determined by the amount of the sample applied, the absorption capacity of the absorption pad and/or the chromatographic time.

In other aspect, the present disclosure provides a cartridge for a lateral flow assay accommodating the strip according to the present disclosure, which comprises a base member comprising a strip receiving part accommodating the strip, and a sample receiving well extended from the strip receiving part formed at one end of the base member; and a cover member for covering the base member, the cover member comprising a sample inlet and a measurement window formed thereon, wherein the sample receiving well is formed at a position of the base member that is perpendicular or corresponds to the sample inlet when the cover member closes the base member.

In one embodiment, the cartridge further comprises at least one guide formed at a position inside or underneath of the cover member facing the strip, the position is selected from the group consisting of a first position perpendicular or corresponds to an area of the sample receiving well where the slant of the subpad is located when the cover member covers the base member; a second position perpendicular or corresponds to an area where the boundary of the slant and the body portion of the subpad is located when the cover member covers the base member; a third position perpendicular or corresponds to an area where the boundary of the sample pad and the body portion of the subpad is located when the cover member covers the base member; and a fourth position perpendicular or corresponds to an area where the boundary of the sample pad and the chromatographic medium is located when the cover member covers the base member.

In other embodiment, the cartridge comprises two guides at the second and the fourth positions.

In still other embodiment, the guides take the form of a dam or a protrusion.

In still other embodiment, the cover member further comprises a ventilation window located between the sample inlet and the measurement window of the cover member.

In still other embodiment, the cartridge further comprises a cover for the measurement window for opening or closing the measurement window.

Advantageous Effects

According to one or more embodiments of the present invention, the present strip allows a new way of loading aqueous sample to the strip providing accurate and reproducible results, which are not influenced by the differences or variations in the amount of sample applied which arise from various reasons or inevitable errors such as pipetting errors. The amount of sample applied can also be conveniently changed as needed without causing inaccuracy or variations in the results within the capacity provided by the sample receiving well.

With the present strips, the sample is first applied or loaded to a sample well provided by a cartridge not like the conventional strips in which the sample is directly loaded or applied onto the strip itself. In the sample well, the sample comes in contact with the subpad of the present strip from which the sample flows to the other part of the strip by a capillary action. In such a way, samples do not need to be measured as accurately as one microliter scale. As long as it meets a minimum volume enough to be in contact with the subpad, constant amount of sample gets to be loaded onto the strip, which leads to an accurate and reproducible result. In addition, for the same reason, the minimum volume may be changed conveniently without the accompanying changes in the cartridges or strips leading to cost savings and improved user convenience.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1A:
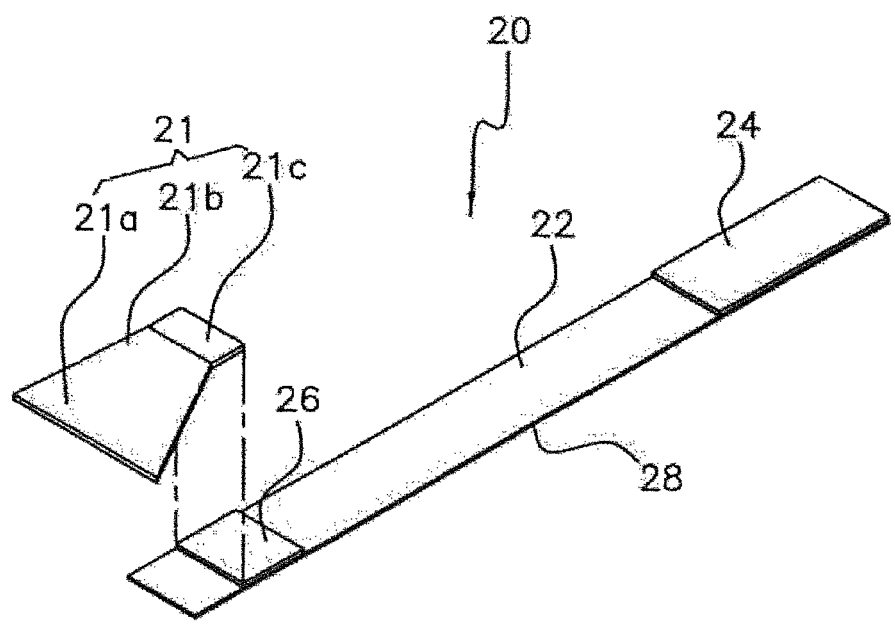
FIG. 1A is a perspective view of the strip with a subpad in which the subpad is configured to be detached from the sample pad according to one embodiment.

Reference will now be made in detail to the present embodiments, examples of which are illustrated in the accompanying drawings, wherein like reference numerals refer to the like elements throughout.

Figure 1B:
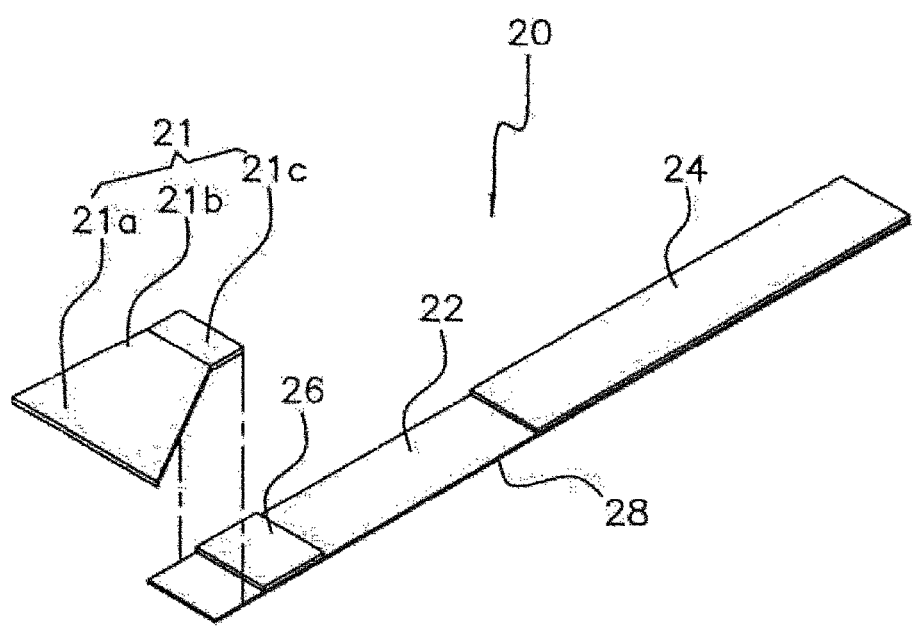
FIG. 1B is a perspective view of the strip with a subpad in which the subpad is configured to be detached from the sample pad according to other embodiment in which the strip has an absorption pad that is longer than the one exemplified in FIG. 1A.
Figure 2A:
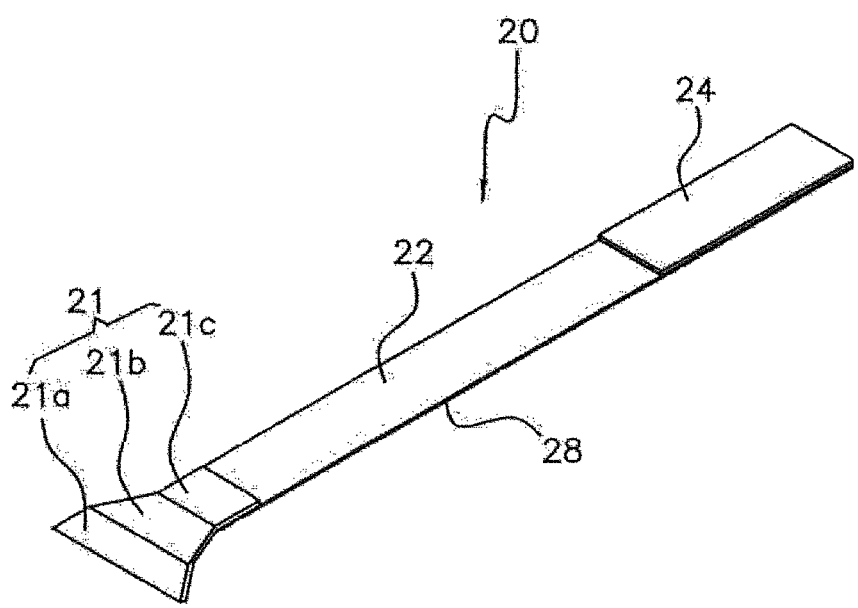
FIG. 2A is a perspective view of the strip with a subpad in which the subpad is configured to be integrated with the sample pad according to one embodiment.
Figure 2B:
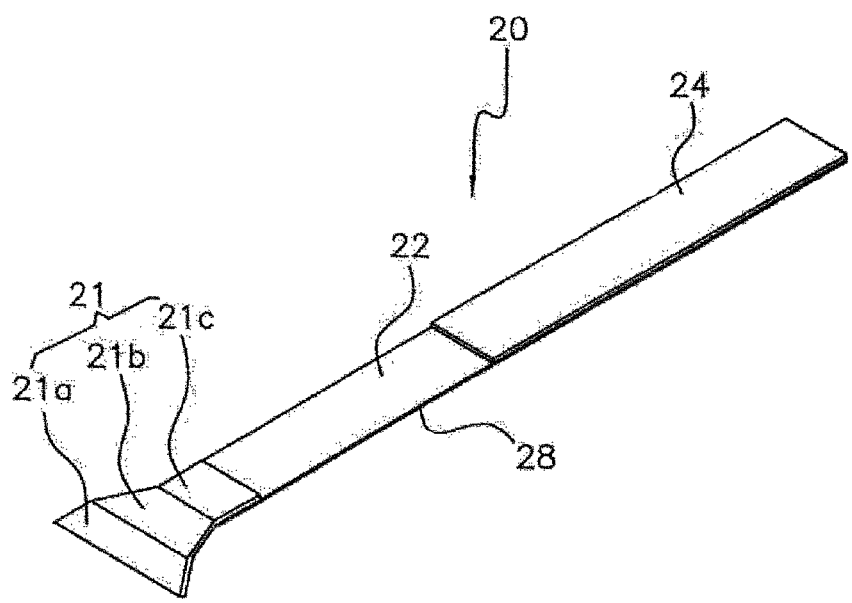
FIG. 2B is a perspective view of the strip with a subpad in which the subpad is configured to be integrated with the sample pad according to other embodiment in which the strip has an absorption pad that is longer than the one exemplified in FIG. 2A.

FIGS. 1A and 1B are perspectives views of the strip with a subpad in which the subpad is configured to be detached from the sample pad according to one embodiment. FIGS. 2A and 2B are perspective views of the strip with a subpad in which the subpad is configured to be integrated with the sample pad according to one embodiment.

As shown in FIGS. 1 and 2, the later flow strip (20) according to one embodiment of the present disclosure comprises a solid support (28), a chromatographic medium (22), a sample pad (20) with a subpad (21) and an absorption pad (24) in which the chromatographic medium, the sample pad with a subpad and the absorption pad are located on the solid support with the sample pad and the absorption pad each being located on each one end of the support with the chromatographic medium being located between the sample pad and the absorption pad in the same plane so as to permit a capillary flow communication.

Referring to FIGS. 1 and 2, the subpad comprises a body portion (21a), a slant (21b) extended from the body portion and a dipping portion (21c) extended from the slant. When the solid support is employed, the chromatographic medium, the absorption pad, the sample pad and the body (21a) of the subpad are positioned on the support in the same plane so as to permit a capillary flow communication. As described hereinafter, when the subpad and the sample pad are configured to be integrated into one, the body portion (21a) of the subpad may act as a sample pad, in which case, the subpad may be longer in length compared to the subpad which is detachable from the sample pad, and the subpad may be made of the same material as is used for the sample pad.

The lateral flow assay for which the present strip is used is a method to analyze the analytes comprised in samples, such as biological samples (300). For example the methods include a quantitative or qualitative detection of nucleic acids or proteins of interest in a sample by an antigen-antibody reaction or a sequence specific hybridization of nucleic acid sequences where the sample moves through the chromatographic medium (nitrocellulose membrane) and the analytes in the sample sequence specifically hybridize to or binds to capture molecules, i.e., particular oligonucleotides or particular antigen and/or antibody, which are immobilized at particular sites of the chromatographic medium.

The term as used herein "adjacent" or "being adjacent" means the sample pads, chromatographic medium and absorption pad touches or are overlapped each other at their ends so that liquid flows through the strip by a capillary action. In one embodiment, the chromatographic medium comprises two ends at each side of the left and right thereof. The one end of the chromatographic medium touches the one end of the absorption pad on at one side of the strip and the other end of the chromatographic medium touches the one end of the sample pad (or one end of the body of the subpad) at the other side of the strip. In other embodiment, one end of the chromatographic medium may be overlapped with one end of the absorption pad, and/or the other end may be overlapped with one end of the sample pad. In still other embodiment, one end of the chromatographic medium is overlapped with one end of the absorption pad, and the other end touches one end of the sample pad or vice versa. When the ends are adjacent to each other by touching, it is preferred that the sample pad, absorption pad and chromatographic medium are substantially of the same thickness.

The term "sample" as used herein refers to a compound or a composition containing analytes to be assayed. In one preferred embodiment, the sample is liquid or an aqueous such as blood including whole blood, plasma and serum or saliva and the like which when applied to the sample pad moves through the chromatographic medium to the absorption pad by a capillary action.

The term "analyte" or "target analyte" or "target material" as used herein refers to a compound of interest being analyzed in a sample and is also called "target material" and includes nucleic acids or proteins. The term "nucleic acids" as used herein refers to any DNA or RNA molecules which are derived from biological materials or synthesized or amplified by known method such as Polymerase Chain Reaction, and includes but not limited to such as genomic DNA (deoxyribose nucleic acid), cDNA, RNA (Ribose Nucleic Acids). Further the nucleic acids may be double stranded or single stranded and can be extracted from the biological materials such as cells and tissues or be synthesized in accordance with the methods known in the art. In one embodiment, the nucleic acids The solid support (28) supports all the other components of the strip, i.e., a sample pad, a chromatographic medium and an absorption pad, or when it is not used, the chromatographic medium (22) per se can function as a support. The support is typically made of water insoluble, nonporous and/or rigid material and has a dimension equal to or larger than the dimension of other elements assembled on the support.

The support may be prepared from various natural and synthetic organic and inorganic materials, as long as that the support does not prevent or interfere with the capillary flow through the strip and interfere with the interaction between the target analyte and the capture molecules on the strip in addition to no non-specific binding to the analytes. Illustrative examples of the materials which may be used for the present support include, but are not limited to, polyethylene, polyester, polypropylene, poly(4-methylbutene), polystyrene, polymethacrylate, poly(ethylene terephthalate), nylon, poly(vinyl butyrate), glass, ceramic, metal and the like. The other components of the strips can be attached to the support by various means including such as adhesives. Proper selection of adhesives may improve the performance of the strip and lengthen the shelf life of the strip. An adhesive which may be used in accordance with the present disclosure includes but is not limited to pressure-sensitive adhesive (PSA). Typically the attachment between the support and the other components of the strip is accomplished as the adhesive penetrates into the pores of the other components, thereby binding them together on the support. This ability of an adhesive to flow under normal conditions is referred to as "cold flow". Since no heat is applied when applying PSA on to the strip components, cold flow of a certain level is indispensable for binding between the strip components. If the level of cold flow is too low, the initial binding force become low, causing insufficient binding between the strip components. In contrast, if the level of cold flow is too high, the adhesive migrates into the other components of the strip and may cause clogging of the pores, formation of hydrophobic spots or redampening of the strip. Such problems associated with the cold flow of the adhesive can be solved by using a direct-casting of membranes. For example, in the direct-casting, a supporting plastic sheet prevents the adhesive from entering into the pores of the membrane and thus vertical migration of the adhesive is prevented during storage.

The sample pad (20) is positioned at one end of the strip; one end of the sample pad is adjacent to one end of the chromatographic medium on its right in the direction of the sample movement. The present sample pad comprises a subpad (21). The subpad is made of a material which is able to move the liquid sample through the strip by a capillary flow. The subpad is divided into or composed of a body portion (21a), a slant extended from the body (21b) and a dipping portion extended from the slant (21c). The body portion (21a), slant (21b) and dipping portion (21c) may be defined by its physical structure and/or functional characteristics. That is, the dipping portion (21c) is a part that comes in contacts with the sample in the sample receiving well. The body portion (21a) is a part that is located on the support (28), and the slant (21b) is a part that is not located on the support but is not directly in contact with the sample. In this context, the boundary between the dipping portion (21c) and the slant (21b) may not be physically present or visible as shown in FIG. 1 or a bending line may be formed on the boundary as far as it does not interfere with a capillary action as shown in FIG. 2.

The sample pad and subpad may be configured in an integrated form or in a form which can be detached from each other. In the integrated form, the body portion (21a) may replace the sample pad and function as a sample pad. In the detachable form, the sample pad is present in which case one end of the sample pad is adjacent to one end of the body portion of the subpad.

In other embodiment, the sample pad and the subpad are configured to be integrated, in which case the subpad and sample pad may be made of the same or different materials. In the detachable form, the subpad may function as a filter unit and thus be made of a material having a filtering capability. The term filtering means to remove impurities in samples to be analyzed such as insoluble materials or other components which are unnecessary for the assay or may reduce the sensitivity or reproducibility of the assay. For example, when whole bloods are used as a sample, the hemoglobin contained in the sample is removed by the filtering, which can positively affect the analysis result. In this perspective, the subpad or sample pad of the present disclosure may be made of a material having a filtering function such as filter paper made of cellulose or glass fibers without being limited thereto.

The sample pad plays a role of receiving the sample comprising analytes of interest. It has a minimum binding capacity towards nucleic acids or proteins and thus allows and/or facilitates the analytes in the sample to flow through the chromatographic medium. The sample pad comprises or is provided with a subpad. The subpad (21) according to the present disclosure contacts with or touches the liquid sample through a dipping portion (21c). It will generate or initiate a capillary flow and thus at least part of the dipping portion is immersed in the sample in a depth, which is enough to generate or initiate a capillary flow through the chromatographic medium to the absorption pad. When the dipping portion touches the sample, the liquid is absorbed to the subpad such that the capillary flow is initiated. That is, the sample absorbed to the dipping portion flows through the slant (21b), the body portion (21a), the sample pad adjacent to the body portion, and chromatographic medium to the absorption pad, which ends the capillary flow by absorbing the liquid sample transferred. During the movement, the analytes in the sample bind specifically and thus is captured to the antigens or antibodies or nucleic acids immobilized on the medium and the unbound ones continues to move through the medium to the absorption pad.

Figure 7:
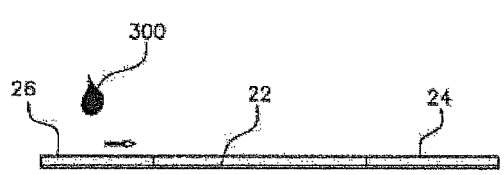
FIG. 7 is schematic diagrams showing the conventional way of loading sample to a strip (a) and the way of loading sample using the strip with a subpad according to one embodiment, in which the arrow indicates the direction of sample movement.
Figure 7:
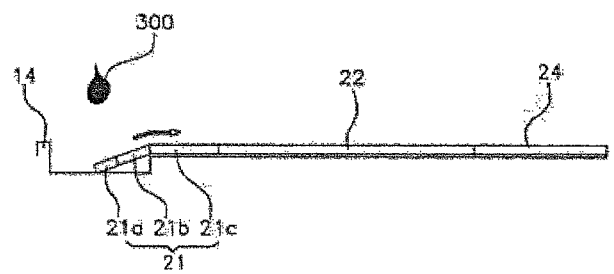

FIG. 7 is schematic diagrams showing the conventional way of loading sample to a strip (a) and the present way of applying sample to the strip employing a subpad according to the present disclosure. In the conventional cases, samples are directly loaded onto a strip in which case error may be occurred due to the differences or variations in the amount of sample loaded from one user to another and even within one user, which leads to inaccurate and/or unreproducible results. The conventional case causes additional inconvenience to the user due to the fixed amount of volume employed for the assay and thus requires a new cartridge for the strip when the volume needs to be increased or changed.

In contrast, the strip according to the present disclosure, the samples are not loaded directly to the sample pad. Instead the samples are loaded to a sample receiving well (12) formed on the cartridge as described in hereinafter. The loaded samples are then contacted with the dipping portion of the subpad through which the samples flow by capillary action through the sample pad, the chromatographic medium and to the absorption pad. Such methods of loading sample according to the present disclosure employing the subpad depend on the absorption force of the subpad for loading of the sample to the sample pad. It will allow the accurate and consistent amount of sample to be used for the analysis as long as the minimum amount of sample is loaded to the sample receiving well without the need of measuring the sample as accurately as one microliter level. This leads to accurate and reproducible results in addition to the amount of sample employed may be changed conveniently without altering the cartridge used.

The sample pad and the subpad may be configured as being integrated or being detached. The integrated one takes a form in which the body portion of the subpad forms the sample pad. The detached one takes a form in which a sample pad is located adjacent to the body portion. In one embodiment, the integrated forms are utilized.

The dipping portion of the subpad of the present disclosure may have a width, which is wider than that of the strip. For example, the subpad has a width, which gradually increases from the slant to the dipping portion, in which case, the area of the dipping portion with which the sample is contacted is increased and thus the filtering capacity may also be increased accordingly.

In other embodiment, the boundary of the dipping portion and the slant and/or the boundary of the slant and the body portion may be bended if needed. The bending means pressing the corresponding portion of the subpad to form a line at the boundary with a condition that the line does not interfere with the capillary flow.

The subpad and/or sample pad may be configured to have a filtering function to remove insoluble particles or other impurities. In this perspective, the subpad or sample pad of the present disclosure may be made of a material having a filtering function such as a filter paper made of cellulose or glass fibers. In one embodiment, the subpad or sample pad is made of cellulose fibers such as Millipore cellulose fiber sample pad material (Cat# CFSP223000). It is preferred that the subpad or sample pad is pretreated to prevent the nonspecific binding of the nucleic acids in the sample thereto and also to facilitate the movement of the components in the sample by capillary flow through the chromatographic medium so that the sensitivity of the assay is achieved at a desired level. In one embodiment, the subpad or sample pad is pretreated with surfactants or inactive proteins, the examples of which include 0.1 M Tris buffer (pH 6 to 9) containing 0.1 to 10% by weight of bovine serum albumin and 0.1% to 10% by weight casein solution for the inactive proteins, and Triton™ X-100 and Tween 20® for the surfactants. The appropriate materials for the pretreatment may be selected considering the types of samples employed or analytes of interest and the pretreatment may be performed at high temperature in a vacuous condition.

The chromatographic medium (22) has two ends, one each on its left and right sides and is in capillary flow communication with the sample pad and absorption pad. The one end is adjacent to the sample pad (21) and the other end is adjacent to the absorption pad (24). The chromatography medium may be supported or backed by the solid support (26), in which case it can attach to the support as described above, or it may serve as a solid support per se. Materials that can be used as the chromatographic medium includes any materials which can allow the liquid in a fluid sample and the analyte, particularly nucleic acids therein to be transferred through the material via capillary action to arrive at and have interactions with the capture molecule immobilized thereon. Typically, the chromatography medium refers to a porous material, which can allow a capillary flow to be generated by aqueous solution. The chromatographic medium which, may be used for the present disclosure include but is not limited to for example, cellulose, nitrocellulose, polyethersulfon, polyvinylidine fluoride, nylon, charged nylon, ceramics and polytetrafluoroethylene. In one embodiment, nitrocellulose is used for the chromatographic medium, the pore diameter of which is at least 0.1 µm, particularly at least about 1.0 µm, more particularly about 0.2 µm to about 20 µm, most particularly about 0.2 µm to about 12 µm. In cases where particulate materials are used as labeling means, the pore size should be at least 10 times the size of the particulate used. Other example includes ceramic materials. The chromatography medium may be multifunctional or be modified to be multifunctional to covalently bind to the capture molecules. A preferred chromatography medium which can be used for the present disclosure includes Prima 60, 85, AE98, AE99 and AE100 from Schleicher & Schuell Bioscience Inc.; HiFlow Plus HF09004, HF13504, HF090, HF120, HF135, HF180 and HF240 from Millipore; and CN90, CN140 from Sartorius AG.

The absorption pad of the present disclosure is positioned being adjacent to one end of the chromatographic medium. The absorption pad is to physically absorb any residual liquid flowed through and to remove any unreacted materials, if any, which has passed through the sample pad and chromatographic medium by a capillary action. The absorption pad which is positioned at one end of the strip controls or promotes the speed of capillary movement by which the analytes and liquid sample are transferred and also works as a reservoir to keep the aqueous sample. The flow speed of the sample may vary depending on the size and quality or capacity of the absorption pad used. An illustrative example of the absorption pad which may be used for the present disclosure includes nitrocellulose, cellulose ester, glass (for example, borosilicate glass fiber), polyethersulfon, cotton, dehydrated polyacrylamide, silica gel, and polyethylene glycol and the like. The speed of capillary flow may be selectively controlled by a suitable selection of the absorption pad employed.

To improve the detection sensitivity, the absorption pad is configured to have a capacity to keep about 70 to 85% of the aqueous sample. Thus when the sample volume changes, the length or the absorption capacity of the absorption pad needs to be adjusted accordingly. Referring to FIGS. 1 and 2, the length of the absorption pad may vary, which also may be determined considering the volume of the sample used and total analysis time.

Figure 3:
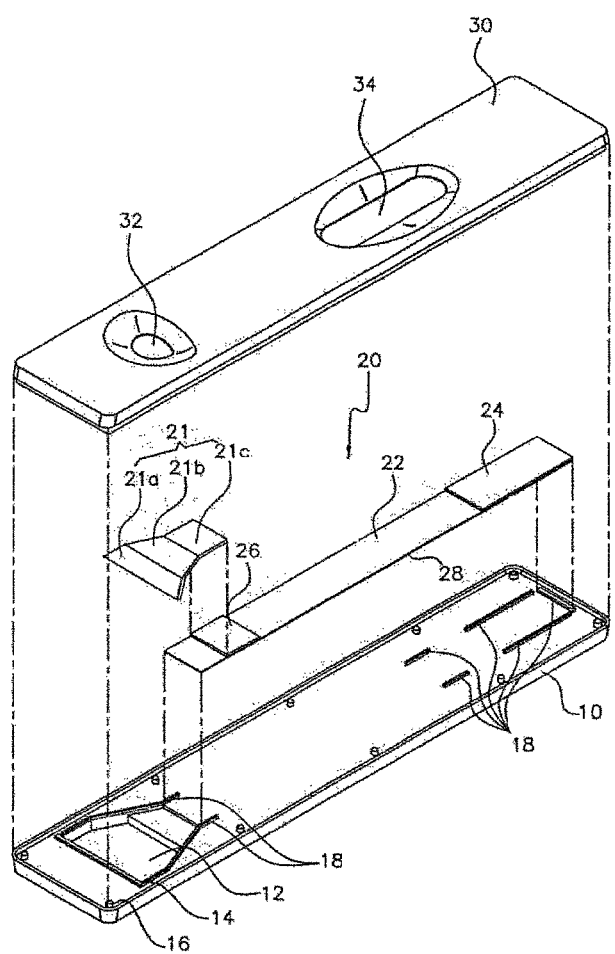
FIG. 3 is an exploded perspective view of a cartridge comprising the strip with a detachable form of a subpad according to one embodiment.
Figure 4:
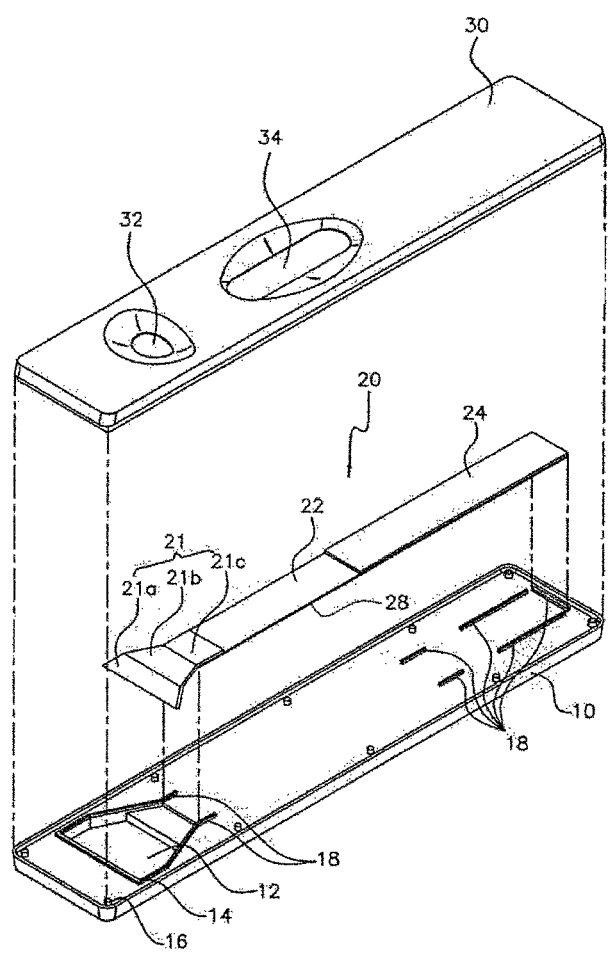
FIG. 4 is an exploded perspective view of a cartridge comprising the strip with an integrated form of a subpad according to one embodiment.
Figure 5:
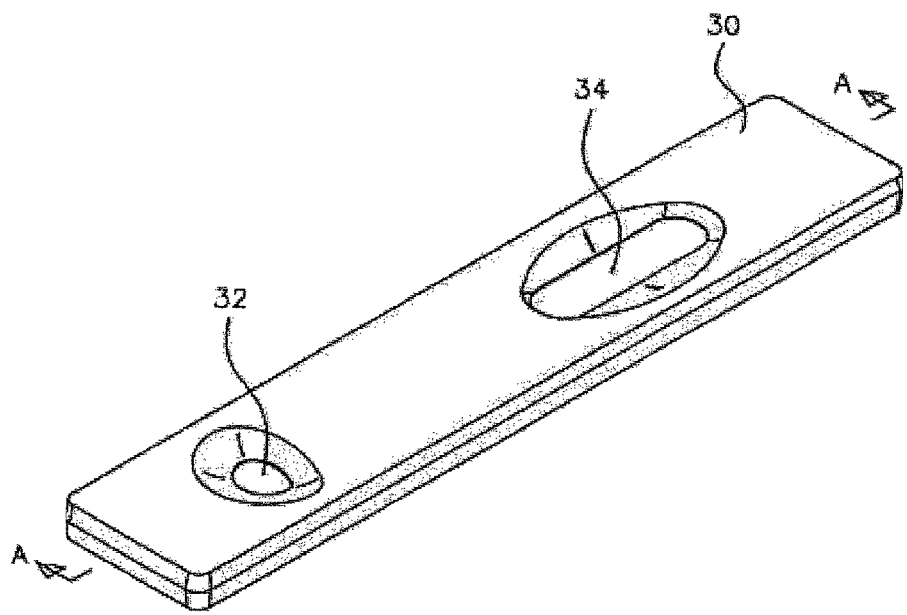
FIG. 5 is a perspective view of a cartridge in a closed state according to one embodiment.
Figure 6:
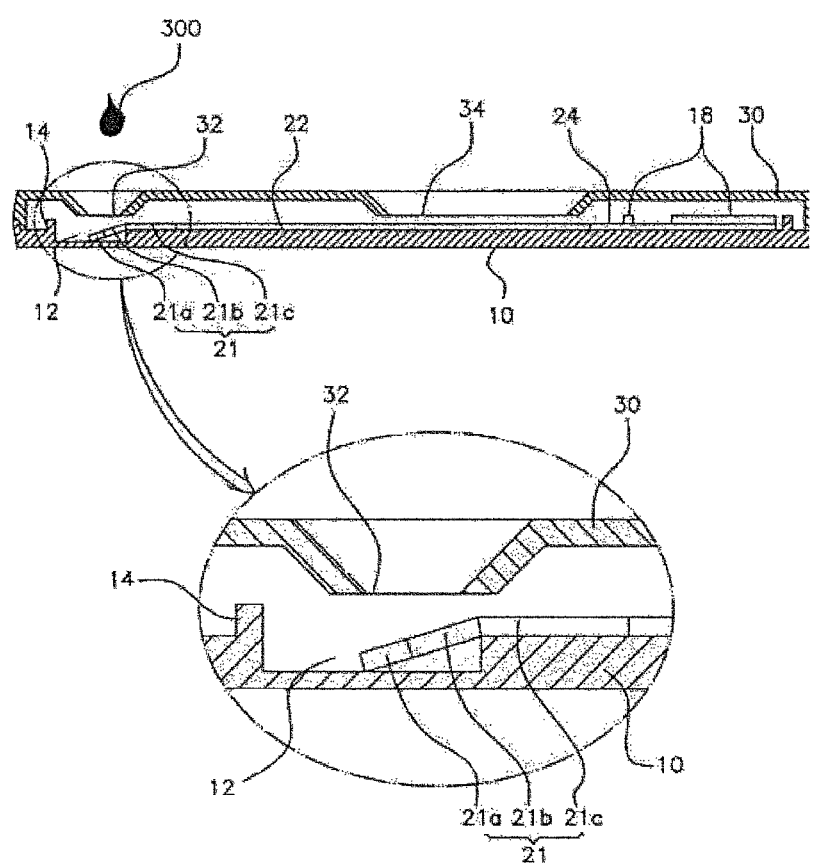
FIG. 6 is a cross-sectional view taken along the line 'A-A' of FIG. 5.
Figure 8:
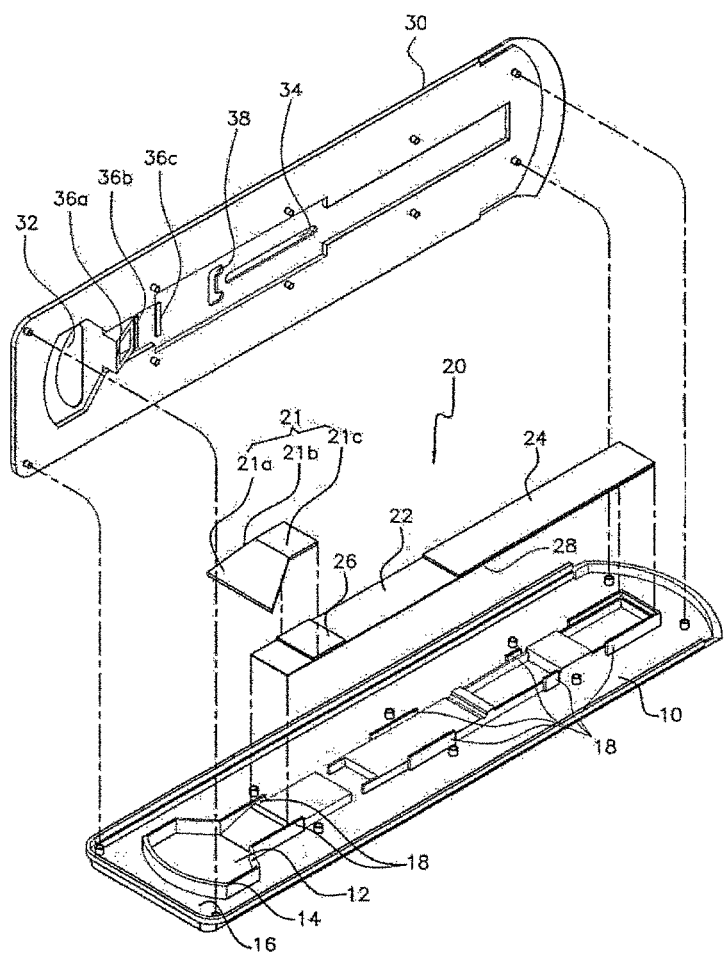
FIG. 8 is an exploded perspective view of a cartridge comprising the strip with a detachable form of a subpad and a cover member in which the guides are formed according to one embodiment.
Figure 9:
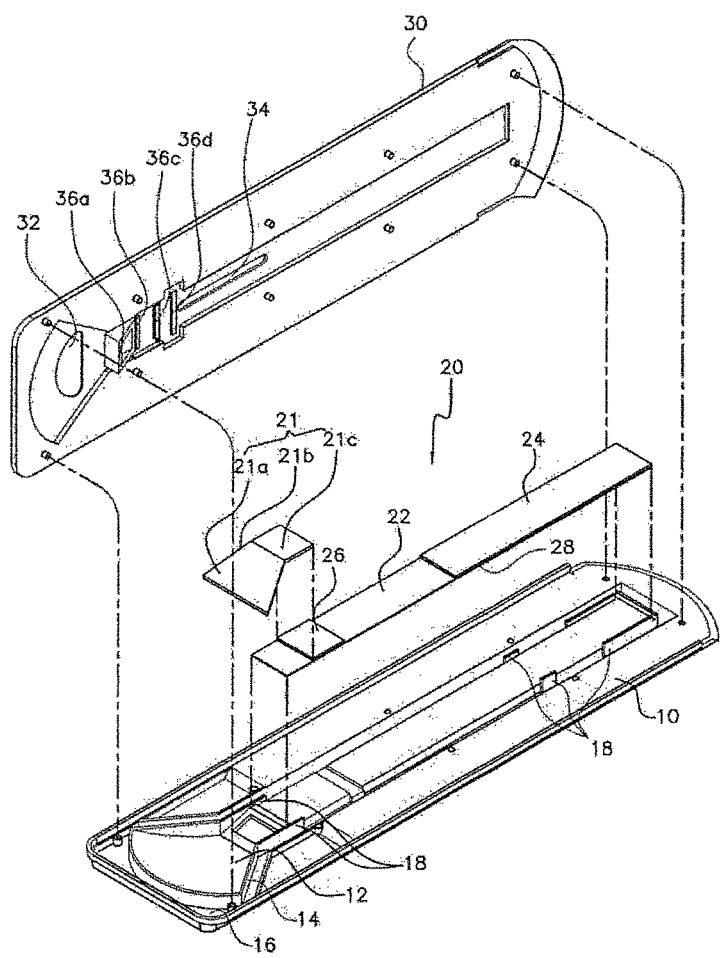
FIG. 9. is an exploded perspective view of a cartridge comprising the strip with a detachable form of a subpad and a cover member in which guides are formed according to other embodiment.
Figure 10:
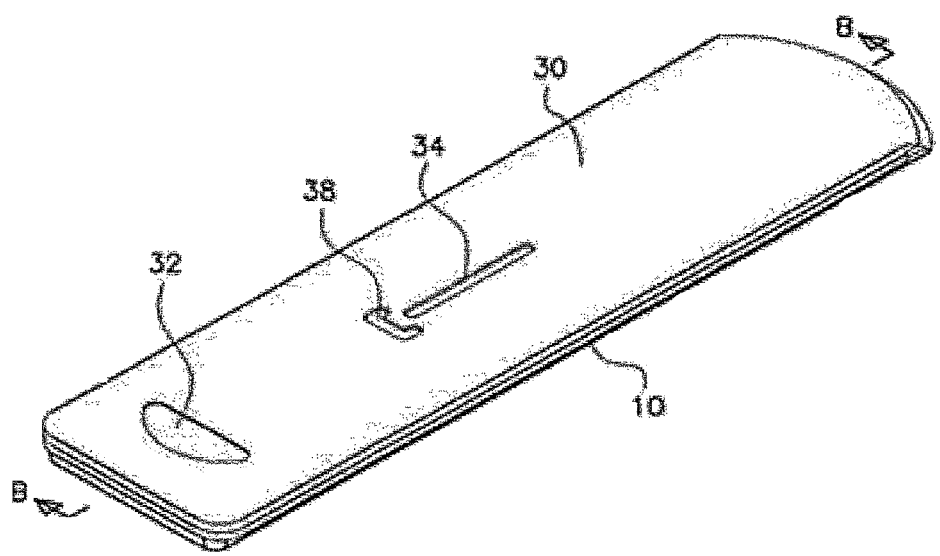
FIG. 10 is a perspective view of a cartridge in a closed state according to one embodiment.
Figure 11A:
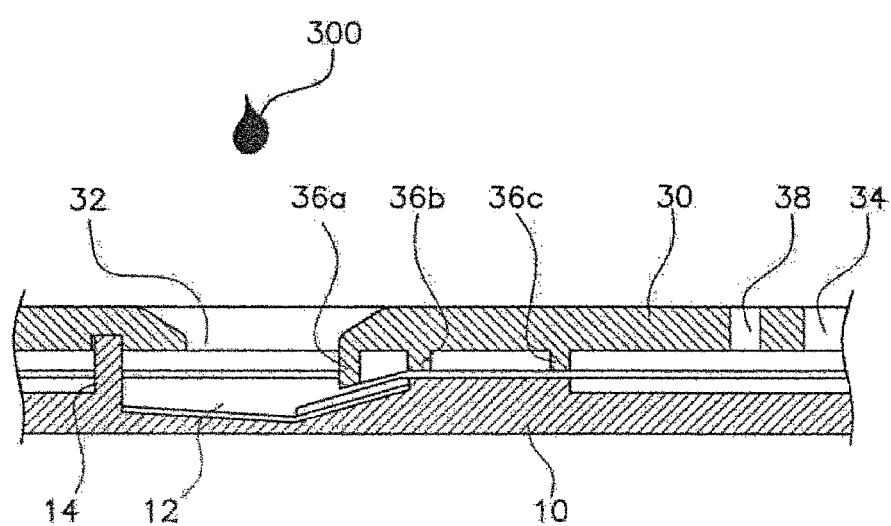
FIG. 11A is a cross-sectional view taken along the line 'B-B' of FIG. 10 in one embodiment in which the cover member comprises the guides corresponding to FIG. 8.
Figure 11B:
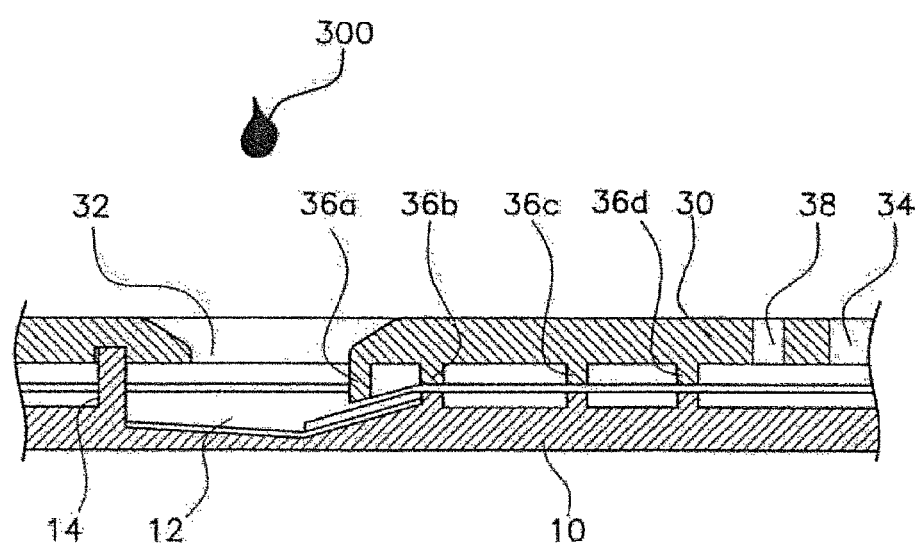
FIG. 11B is a cross-sectional view taken along the line 'B-B' of FIG. 10 in one embodiment in which the cover member comprises the guides corresponding to FIG. 9.

In other aspect, the present disclosure relates to a cartridge for later flow assay, which is used with the present strip. FIG. 3 is an explode perspective view of a cartridge comprising a strip with a detachable form of a subpad according to one embodiment of the present disclosure. FIG. 4 is an explode perspective view of a cartridge comprising a strip with an integrated form of a subpad according to one embodiment of the present disclosure. FIG. 5 is a perspective view of a cartridge in a closed state according to one embodiment of the present disclosure. FIG. 6 is a cross-sectional view taken along the line 'A-A' of FIG. 5 in one embodiment of the present disclosure. FIG. 7 is schematic diagrams showing the conventional way of loading sample to a strip (a) and the present way of loading sample to a strip employing subpad (b). FIG. 8 is an explode perspective view of a cartridge comprising a strip with an detachable form of a subpad according to one embodiment and a cover member in which guides are formed according to one embodiment. FIG. 9 is an explode perspective view of a cartridge comprising a strip with an detachable form of a subpad according to other embodiment and a cover member in which guides are formed according to other embodiment. FIG. 10 is a perspective view of a cartridge in a closed state according to one embodiment. FIG. 11A is a cross-sectional view taken along the line 'B-B' of FIG. 10 in one embodiment in which the cover member comprise the guides corresponding to FIG. 8. FIG. 11B is a cross-sectional view taken along the line 'B-B' of FIG. 10 in one embodiment in which the cover member comprise the guides corresponding to FIG. 9.

As shown in FIGS. 3 and 4, the present cartridge comprises a base member (10) comprising a strip receiving part (18) and a sample receiving well (12) extended from the strip receiving part formed at one end of the strip receiving part, which are formed on the base member. A cover member (30) which covers the base member, the cover member comprising a sample inlet (32) and a measurement window (34) formed thereon, wherein the sample receiving well is positioned perpendicular or corresponds to the sample inlet when the cover member covers the base member. The strip receiving part further comprises at least one guide to accommodate plurality of strips and to hold the strip in place preventing the movement of the strip.

Referring to FIG. 5, when the cover member (30) is engaged with the base member (10), the cover member (30) and the base member (10) interlock with each other at the protrusion (16) along the rim thereof so that the device becomes waterproof or sealed aerosol proof.

The cartridge for lateral flow assay of the present disclosure is optimized to be used with the present strip having a subpad. In this perspective, the cartridge further comprises the strip of the present disclosure having a subpad consisting of a dipping portion, a slant and a body portion, in which the dipping portion and the slant are positioned on the sample receiving well or sample well formed on the base member of the cartridge.

Referring to FIG. 6, the sample receiving well or sample well (12) is formed at a position on the base member which is perpendicular or corresponds to the sample inlet when the cover member is engaged with the base member. The sample (300) is introduced through the sample inlet to the sample receiving well (12). The sample receiving well further comprises a protruding dam (14) to accommodate the sample. The dipping portion of the subpad (21) is positioned in the sample receiving well so that when the sample is introduced to the sample receiving well, at least part of the dipping portion comes in contact with the sample, and the movement of the sample is initiated by a capillary action. The sample receiving well may take a form of various sizes and shapes, which may be determined considering the types and/or the amount of the sample employed or the dimensions of the subpad employed. The sample receiving well is configured to have a size, which is able to accommodate the amount of the sample that is enough to immerse at least part of the dipping portion. In one embodiment, the sample receiving well may be configured to have a size to accommodate about 50 to 300 microliters of sample.

In one embodiment, the sample receiving well has a bottom that is either flat or inclined as shown in FIG. 11. Referring to FIG. 11, the sample well is configured to have a slope or an incline to accommodate a slant (21b), or slant (21b) and a dipping portion (21c) of the subpad.

Referring to FIGS. 8, 9 and 11, at least one guide (36) is formed on inside or underneath of the cover member (30) facing the strip. The guide may be used to prevent an overflow of the sample from the sample receiving well. In one embodiment, the present cover member has at least one guide formed at one of the following positions of the cover member; a first position which corresponds to the area of the sample receiving well where the slant of the subpad is positioned when the cover member and base member are interlocked; a second position which corresponds to the area where the boundary of the body portion and the slant of the subpad is positioned when the cover member and base member are interlocked; a third position which corresponds to the area where the boundary of the body portion of the subpad and the sample pad is positioned when the cover member and base member are interlocked; and a fourth position which corresponds to the area where the boundary of the sample pad and the chromatographic medium is positioned when the cover member and base member are interlocked. In one embodiment, the cover member comprises guides formed at the second (36b) and the fourth (36d) positions. Referring to FIGS. 8 and 9, the guides at the first and the second positions may be integrated into one and take a form which has a bottom corresponding to the slope of the sample receiving well. Also referring to FIG. 8, when the chromatographic medium and the sample pad are overlapped at their adjacent ends and thus the thickness of the strip increases at the overlapped site which is thus pressed when the cover member and the base member are interlocked, the guide at the fourth position is optional.

The guides may take a form of a protrusion or a dam. Particularly it is preferred that the guide at the second position take a form of a dam to prevent the overflow of the sample in the sample receiving well.

Referring to FIGS. 8 and 10, the cartridge may further comprise a window for ventilation. The ventilation window is to prevent the inhibition of the capillary flow by a force generated by the adherence of the cover member to the strip mediated by the liquid present on the strip. The ventilation window may be omitted if the measurement window is formed to have a width, which is identical to that of the strip employed.

The present way of loading using the subpad and the sample receiving well is differentiated from the conventional process in which the sample is directly deposited on the strip. Therefore, by using the present method, one does not have to measure the sample as precisely as one microliter scale, which results in the user conveniences and reduction in the error associated with the inaccurate measurement leading to a reliable and reproducible result.

The measurement window (34) is a window for detecting or observing the results of the lateral flow assay such as antigen-antibody reaction or nucleic acid hybridization.

In one embodiment, the cartridge may further comprise a cover for the measurement window (not shown), which is to provide a protection for the strip mounted on the cartridge from the damages caused by such as a transportation, humidity, scratch, contamination or inadvertent loading of the sample through the window. The material which may be used for the present strip includes conventional ones such as for example nitrocellulose membrane and the like.

The cartridge according to the present disclosure may be made of a variety of synthetic resins, which are chemically stable or a combination thereof. For example, the present cartridge may be made by fabrication methods known in the art using a variety of thermoplastic or thermosetting plastics such as, without being limited thereto, polyethylene, polypropylene, polystyrene, polyethylene terephthalate, polyamide, polyester, polyvinyl chloride, polyurethane, polycarbonate, polyvinylidene chloride, polytetrafluoroethylene, and polyetherimide, and a combination thereof. Meanwhile, materials for fabricating the present device are not necessarily limited to a specific material or a specific group of material, but any material suitable for the purpose of the present device may also be used.

The cartridge according to the present disclosure may be manufactured using various molding methods known in the art, for example, injection, rotation, extrusion, and/or calendaring methods depending on the type of the material used. In one embodiment of the present disclosure, the cover member and the base member of the device may be made of Acrylonitrile Butadiene Styrene (ABS), and may be manufactured by injection-molding of acryl when a transparent material is used. Those skilled in the art would be able to select materials and methods appropriate for the purpose of the present disclosure from various materials and methods known in the art to manufacture the device according to the present disclosure. In addition to the synthetic resins, various additives for example, fillers, plasticizers, stabilizers, coloring agents, and antistatic agents may also be used as required.

The present cartridge may be manufactured in various shapes and sizes, and in one embodiment, it has a rectangular shape, and may be used with a variety of measuring device or readers that is compatible with the cartridge mounted with the present strip. The reader that may be used with the present cartridge includes, but is not limited to, i-Chroma (Boditech Med Inc.), and RAMP System (Response Biomedical Inc. Canada). The present cartridge may be manufactured in accordance with the readers, which are used for a lateral flow assay.

The target molecules which may be measured by a lateral flow assay using the present strip includes various biological materials including, but not limited to, hsCRP (high sensitivity C-reactive protein), HbA1c (glycated hemoglobin), microalbumin, PSA (prostate specific antigen), AFP (Alpha-fetoprotein), and cTnI (cardiac Troponin I).

While a few exemplary embodiments of the present invention have been shown and described, it would be appreciated by those skilled in the art that changes may be made to these exemplary embodiments without departing the principles and spirit of the invention, the scope of which is defined by the claims and their equivalents.

DESCRIPTION OF THE NUMERALS USED

10: Base member
12: Sample receiving well
14: Protruding dam
16: Protrusion
18: Strip receiving part
20: Strip
21: Subpad
21a: Dipping portion; 21b: Slant; 21c: Body portion
22: Chromatographic medium
24: Absorption pad
26: Sample pad
28: Solid support
30: Cover member
32: Sample inlet
34: Measurement window
36a: First guide; 36b: Second guide; 36c: Third guide; 36d: Fourth guide
38: Ventilation window
300: Sample

What is claimed is:

1. A cartridge for a lateral flow assay accommodating a strip comprising:
   a base member comprising a strip receiving part accommodating the strip, and a sample receiving well extended from the strip receiving part formed at one end of the base member; and
   a cover member comprising a sample inlet and a measurement window, the cover member covering the base member,
   wherein the sample receiving well is formed at a position that is corresponds to the sample inlet when the cover member covers the base member, wherein the strip comprises a solid support, a chromatographic medium, a sample pad with a subpad comprising a body portion, a slant extended from the body portion and a dipping portion extended from the slant, and an absorption pad; the chromatographic medium, the sample pad and the absorption pad being positioned on the solid support; the sample pad and the absorption pad each being positioned on each end of the solid support with the chromatographic medium located therebetween in such a way that one end of the chromatographic medium is adjacent to one end of the sample pad and the other end of the chromatographic medium is adjacent to one end of the absorption pad;

wherein the cover member comprises three guides formed at a second position, a third position and a fourth position inside the cover member facing the strip, the second positon corresponding to an area where the boundary of the slant and the body portion of the subpad is located when the cover member covers the base member; the third position corresponding to an area where the boundary of the sample pad and the body portion of the subpad is located when the cover member covers the base member; and the fourth position corresponding to an area where the boundary of the sample pad and the chromatographic medium is located when the cover member covers the base member.

2. The cartridge of claim 1, further comprising a guide formed at a first position inside the cover member facing the strip, the first position corresponding to an area of the sample receiving well where the slant of the subpad is located when the cover member covers the base member.

3. The cartridge of claim 1, wherein the guides takes the form of a dam or a protrusion.

4. The cartridge of claim 1, wherein the cover member further comprises a ventilation window located between the sample inlet and the measurement window.

5. The cartridge of claim 1, further comprising a cover for the measurement window for opening or closing the measurement window.

* * * * *